United States Patent [19]

Jones, Jr. et al.

[11] 4,028,319

[45] June 7, 1977

[54] 2 AND 3-SUBSTITUTED ENKEPHALINS

[75] Inventors: David A. Jones, Jr., Evanston; James M. Schlatter, Glenview; Richard A. Mikulec, Chicago; Judith A. Reuter, Skokie; Robert H. Mazur, Deerfield, all of Ill.

[73] Assignee: G. D. Searle & Co., Chicago, Ill.

[22] Filed: May 7, 1976

[21] Appl. No.: 684,321

[52] U.S. Cl. .......................... 260/112.5 R; 424/177
[51] Int. Cl.² ........................................ C07C 103/52
[58] Field of Search ............................ 260/112.5 R

[56] References Cited
OTHER PUBLICATIONS

Nature; 260, (1976) pp. 624 and 625.
Chem. Abst., 85, (1976) 117125r.
Nature; 258 (1975) 577–579.

*Primary Examiner*—Delbert R. Phillips
*Attorney, Agent, or Firm*—Michael T. Murphy; John J. McDonnell

[57] ABSTRACT

Analogs of enkephalin having agonist activity at opiate receptors are disclosed herein. These analogs are useful as analgesics, non-addicting narcotic antagonists and anti-diarrheal agents.

23 Claims, No Drawings

2 AND 3-SUBSTITUTED ENKEPHALINS

BACKGROUND OF THE INVENTION

This invention relates to analogs of enkephalin which display agonist activity at opiate receptors. Enkephalin, a naturally occurring pentapeptide, has been isolated and found to be a mixture of two pentapeptides which differ only in the amino acid present at the 5-position. Leucine[5]-enkephalin is thus represented by the following structural formula

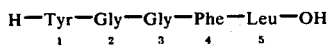

and methionine[5]-enkaphalin by the following formula

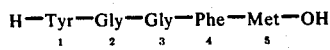

wherein the Tyr, Met and Leu residues are all of the L-stereochemical configuration.

SUMMARY OF THE INVENTION

The present invention is concerned with novel analogs of Leucine[5]-enkephalin and methionine[5]-enkephalin. More particularly, this invention is concerned with enkephalin analogs of the formula

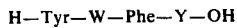  (I)

wherein Y represents Leu or Met; W is selected from the group consisting of
—Aib—Gly—,
—Ala—Gly—,
—Sar—Gly—,
—Gly—Aib—,
—Gly—Ala—,
—Gly—Sar—,

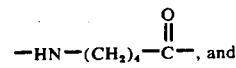

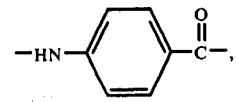

and the stereochemical configuration of each of the optically active amino acid residues is D, L or DL.

Preferred compounds of this invention are those of the formula

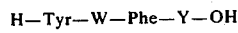  (II)

wherein W and Y are as defined hereinbefore and the stereochemical configuration of each of the optically active amino acid residues is L.

Particularly preferred compounds of this invention are those of the formulas

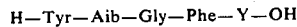  (III)

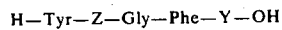  (IV)

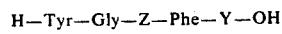  (V)

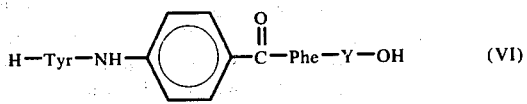  (VI)

wherein Y is as defined hereinbefore.

Z represents Ala or Sar, and the stereochemical configuration of each of the optically active amino acid residues is L.

Abbreviations connote the amino acids defined in accordance with the nomenclature rules published by the IUPAC-IUB Commission on Biochemical Nomenclature in *Biochem. J.*, 126, 773–780 (1972). The amino acids have the L-stereochemical configuration unless otherwise indicated.

Equivalent to the enformulated compounds for the purposes of this invention are solvates thereof in which biologically insignificant amounts of solvent are present.

Also equivalent to the compounds of formula (I) for the purposes of this invention are the pharmaceutically acceptable acid addition salts thereof. Such acid addition salts can be derived from a variety of inorganic and organic acids such as sulfuric, phosphoric, hydrochloric, hydrobromic, hydriodic, nitric, sulfamic, citric, lactic, pyruvic, oxalic, maleic, succinic, tartaric, cinnamic, acetic, trifluoroacetic, benzoic, salicylic, gluconic, ascorbic and related acids.

DETAILED DESCRIPTION OF THE INVENTION

The compounds of the present invention are useful in consequence of their valuable pharmacological properties. They are, for example, agonists at opiate receptor sites. Such agonists are useful as analgesics, narcotic antagonists and anti-diarrheal agents.

The assay utilized for detection of the agonist activity at opiate receptor sites is a modification of the technique described by Pert, Snowman and Snyder, in *Brain Research*, 70, 184 (1974).

Details of that assay are as follows: Guinea pigs weighing 600–700 grams are killed and the whole brains removed and homogenized in 0.32 M sucrose after removal of the cerebella. The homogenate is centrifuged at 1000 × g. for 10 minutes. The pellet is osmotically shocked with ice-cold water and recentrifuged at 10,000 × g. for 10 minutes. The resultant supernatant, containing the membrane fraction used for the binding assay, is diluted with 0.06 M Tris buffer (pH 7.4 at 25° C) to a protein concentration of 2 mg/ml.

Aliquots of the final membrane suspension are incubated with varying concentrations of the test compound. Aliquots incubated with $10^{-6}$ M levorphanol are used to determine non-specific binding of the radioactive ligand. The assay is run at 4° C. and is initiated with the addition of 8 mM $^3$H-naloxone (specific activity greater than 20 C/mmole). The reaction is terminated by rapid filtration of the incubation mixture on GF/B glass filter papers. The membranes trapped on the filter paper are washed twice with ice-cold Tris buffer. The amount of radioactive ligand bound is determined by liquid scintillation techniques. An $ID_{50}$ concentration of the $^3$H-naloxone binding is determined from log-probit curves of the percent inhibition of $^3$H-naloxone binding versus concentration of the test compound.

The in vitro assay described is widely known to correlate with relative agonist-antagonist properties in vivo: *Nature*, vol. 247, Jan. 11, 1974. When known agonists-antagonists such as morphine and methadone were tested by this assay, in the absence of sodium ion, they had $ID_{50}$ concentrations of $1.2 \times 10^{-8}$ and $2.4 \times 10^{-8}$, respectively.

It is also known that the receptor affinities in the ileum are similar in their binding characteristics with those of the brain. Lars Terenius, *Acta. Pharmacol. et Toxicol.*, 37, 211–221 (1975). Available evidence indicates that drugs which act on the ileum opiate receptors cause constipation, and are therefore useful as anti-diarrheal agents.

The compounds of formula (I) may be combined with various typical pharmaceutical carriers to provide compositions suitable for use as analgesics, as narcotic antagonists for use in the treatment of drug addiction and as anti-diarrheals. The dosage of these compounds is dependent upon various factors, such as the particular compound employed and the particular response obtained. Typical dosages for use as an analgesic vary from 0.1 to 6.0 mg/kg per day administered parenterally.

The manufacture of the instant novel compounds is conveniently achieved by processes adapted to the synthesis of peptides, i.e., both solution syntheses and solid-phase peptide syntheses. In the case of solution syntheses, the order in which the amino acids are coupled is not critical. Thus, the pentapeptide may be produced by coupling any two suitable units containing the desired amino acids.

A convenient method for preparing the compounds of this invention involves the coupling of a C-terminal dipeptide, optionally substituted with protecting groups, of the formula

H—Phe—Y—OH wherein Y is as defined hereinbefore, with an N-protected active ester of the formula

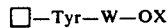

☐—Tyr—W—OX wherein W is as defined hereinbefore, ☐ is an N-protecting group, and X is an active ester group, to give an N-protected peptide of the formula

☐—Tyr—W—Phe—Y—OH        (VII)

The N-blocked peptide of formula (VII) is then deprotected in a conventional manner to afford the desired peptide of formula (I).

The above coupling reaction is conducted in a suitable organic solvent such as methylene chloride, dimethylformamide, or tetrahydrofuran. The use of an organic base, such as N-methylmorpholine facilitates the reaction.

Alternatively, the desired peptide can be obtained by solid-phase peptide synthesis which consists of first attaching to a polymer support, e.g., a chloromethylated copolystyrene 1% divinylbenzene polymer, the optionally N-protected C-terminal amino acid, followed by removal of the N-protecting group, and coupling, in the presence of a suitable reagent, e.g., dicyclohexylcarbodiimide, successively with each of the appropriate N-protected amino acids.

Suitable active esters for use in this invention are those which cause the acid function of the amino acid to become more reactive such as alkyl esters with electron withdrawing (negative) substituents, vinyl esters, enol esters, phenyl esters, thiophenyl esters, nitrophenyl esters, 2,4-dinitrophenyl esters, trichlorophenyl esters, and nitrophenylthiol esters. The use of 2,4,5-trichlorophenyl esters is particularly preferred for the preparation of the present compounds.

The amino functions of the intermediates of this invention may be protected by commonly used amino protecting groups such as aryl-lower alkyl groups, such as diphenylmethyl or triphenylmethyl groups, which are optionally substituted by halogen, nitro, lower alkyl or lower alkoxy, for example; benzhydryl, trityl, and di-paramethoxybenzhydryl; acyl groups, such as formyl, trifluoroacetyl, phthaloyl, p-toluenesulphonyl, benzenesulphonyl, benzenesulphenyl and o-nitrophenylsulphenyl; groups derived from carbonic acid or thiocarbonic acid, such as carbobenzoxy groups which are optionally substituted in the aromatic radical by halogen atoms, nitro groups or lower alkyl, lower alkoxy or lower carbalkoxy groups, for example, carbobenzoxy, p-bromocarbobenzoxy or p-phenylazobenzyloxycarbonyl and p-(p'-methoxyphenylazo)benzyloxycarbonyl, tolyloxycarbonyl, 2-phenyl-2-propoxycarbonyl, 2-tolyl-2-propoxycarbonyl and 2-(parabiphenyl)-2-propoxycarbonyl; and aliphatic oxycarbonyl groups, such as t-butoxycarbonyl, allyloxycarbonyl, cyclopentyloxycarbonyl, t-amyloxycarbonyl. A particularly preferred N-protecting group for use in this invention is the t-butoxycarbonyl group.

The amino groups can also be protected by forming enamines, obtained by reaction of the amino group with 1,3-diketones, for example benzoylacetone, or acetylacetone.

Protecting groups are conveniently removed by reactions such as reduction with sodium in liquid ammonium, hydrogenolysis (for instance, in the presence of a palladium black catalyst), treatment with hydrohalic acid (such as hydrobromic, hydrofluoric or hydrochloric acids) in acetic acid, or treatment with trifluoroacetic acid.

The following examples describe in detail the preparation of compounds illustrative of the present invention. It will be apparent to those skilled in the art that many modifications, both of materials and methods, may be practiced without departing from the purpose and intent of this disclosure. Throughout the examples hereinafter set forth, temperatures are given in degrees Centigrade (° C.) and relative amounts in parts by weight, except as otherwise noted.

EXAMPLE 1

A solution of 21.2 parts N-t-butoxycarbonyl-L-phenylalanine 2,4,5-trichlorophenyl ester and 12.7 parts L-methionine benzyl ester in 200 parts methylene chloride is stirred overnight at room temperature. Completion of the reaction is determined by thin layer chromatography. The solvent is then stripped under reduced pressure and the crude residue subjected to low pressure column chromatography on silica gel. The resulting product, N-t-butoxycarbonyl-L-phenylalanyl-L-methionine benzyl ester, is dissolved in 50 parts dioxane and stirred with a 10 fold excess of 2 N HCl in dioxane for 10 minutes. The solvent is removed by evaporation under reduced pressure. The solid residue, after trituration with ethyl ether, affords pure L- phenylalanyl-L-methionine benzyl ester hydrochloride. This compound is represented by the following formula

H—Phe—Met—OBzl·HCl

EXAMPLE 2

Repetition of the procedure detailed in Example 1 using an equivalent quantity of L-leucine benzyl ester in place of the L-methionine benzyl ester affords L-phenylalanyl-L-leucine benzyl ester hydrochloride. This compound is represented by the following formula

H—Phe—Leu—OBzl·HCl

EXAMPLE 3

A solution containing 19.5 parts N-t-butoxycarbonylglycine 2,4,5-trichlorophenyl ester and 13.8 parts L-alanine benzyl ester in 200 parts methylene chloride is stirred overnight at room temperature. The solvent is then removed by evaporation under reduced pressure and the residue subjected to low pressure column chromatography. The resulting pure N-t-butoxycarbonylglycyl-L-alanine benzyl ester is dissolved in 60 parts dioxane and treated with a ten-fold excess of 2 N HCl in dioxane, with stirring, for 15 minutes. The solvent is again removed by evaporation under reduced pressure and the residue triturated with ethyl ether to afford glycyl-L-alanine benzyl ester hydrochloride. This compound is represented by the following formula

H—Gly—Ala—OBzl·HCl

EXAMPLE 4

When the procedure detailed in Example 3 is repeated using an equivalent quantity of sarcosine benzyl ester in place of the L-alanine benzyl ester, there is obtained glycylsarcosine benzyl ester hydrochloride represented by the following formula

H—Gly—Sar—OBzl·HCl

EXAMPLE 5

19.3 Parts N-t-butoxycarbonyl-L-alanine 2,4,5-trichlorophenyl ester and 9.7 parts glycine benzyl ester are dissolved in 200 parts methylene chloride and the resulting solution is stirred overnight at room temperature. Removal of the solvents under reduced pressure affords crude N-t-butoxycarbonyl-L-alanylglycine benzyl ester which is purified by low pressure column chromatography. The purified blocked dipeptide is then dissolved in 50 parts dioxane and stirred with a 10 fold excess of 2 N HCl in dioxane for 15 minutes. The solvent is removed by evaporation under reduced pressure to give, after trituration with ethyl ether, L-alanylglycine benzyl ester hydrochloride. This compound is represented by the following formula

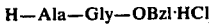
H—Ala—Gly—OBzl·HCl

EXAMPLE 6

Substitution of an equivalent quantity of N-t-butoxycarbonylsarcosine 2,4,5-trichlorophenyl ester for the N-t-butoxycarbonyl-L-alanine 2,4,5-trichlorophenyl ester of Example 5 and substantial repetition of the procedure detailed therein affords sarcosylglycine benzyl ester hydrochloride represented by the following formula

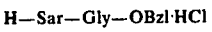
H—Sar—Gly—OBzl·HCl

EXAMPLE 7

A solution of 17.6 parts N-t-butoxycarbonyl-L-tyrosine 2,4,5-trichlorophenyl ester, 9.0 parts glycyl-L-alanine benzyl ester hydrochloride and 1.2 parts N-methylmorpholine in 200 parts methylene chloride is stirred for 16 hours at room temperature. Removal of the solvent under reduced pressure affords a crude product which is purified by low pressure column chromatography to give N-t-butoxycarbonyl-L-tyrosylglycyl-L-alanine benzyl ester. The purified material is dissolved in 400 parts methanol. Then, 0.4 part palladium black metal catalyst is added and the mixture shaken with hydrogen at atmospheric pressure and room temperature for about 5 hours. The catalyst is removed by filtration, and the solvent is removed by evaporation under reduced pressure. The resulting material is purified by low-pressure chromatography to give N-t-butoxycarbonyl-L-tyrosylglycyl-L-alanine. This compound is represented by the following formula

Boc—Tyr—Gly—Ala—OH

EXAMPLE 8

Repetition of the procedure of Example 7 substituting equivalent amounts of glycylsarcosine benzyl ester hydrochloride, L-alanylglycyl benzyl ester hydrochloride or sarcosylglycyl benzyl ester hydrochloride for the glycyl-L-alanine benzyl ester hydrochloride affords N-t-butoxycarbonyl-L-tyrosylglycylsarcosine, N-t-butoxycarbonyl-L-tyrosyl-L-alanylglycine, or N-t-butoxycarbonyl-L-tyrosylsarcosylglycine, respectively.

EXAMPLE 9

11.7 Parts 5-aminopentanoic acid and 22.8 parts p-toluenesulfonic acid monohydrate is suspended in 180 parts benzene and 32.4 parts benzyl alcohol is added. A continuous water separator is attached to the flask and the mixture stirred at vigorous reflux temperature for 16 hours. After cooling to room temperature, the solvent is removed under reduced pressure and the residual oil shaken with n-hexane. The supernatant is discarded and the gummy product rubbed with ethyl ether causing crystallization to take place. The solid is separated by filtration and washed with ethyl ether to afford the desired 5-aminopentanoic acid benzyl ester p-toluenesulfonate.

EXAMPLE 10

Repetition of the procedure detailed in Example 9 using an equivalent quantity of p-aminobenzoic acid in place of the 5-aminopentanoic acid affords p-aminobenzoic acid benzyl ester p-toluenesulfonate.

EXAMPLE 11

Substitution of equivalent amounts of 5-aminopentanoic acid benzyl ester p-toluenesulfonate or p-aminobenzoic acid benzyl ester p-toluenesulfonate for the glycyl-L-alanine benzyl ester hydrochloride of Example 7, and substantial repetition of the procedure detailed therein affords N-t-butoxycarbonyl-L-tyrosyl-5-aminopentanoic acid or N-t-butoxycarbonyl-L-tyrosyl-p-aminobenzoic acid, respectively.

EXAMPLE 12

14.0 Parts N-t-butoxycarbonyl-L-tyrosylglycyl-L-alanine and 3.5 parts N-methylmorpholine are dissolved in 200 parts dimethylformamide and cooled to −15° C.

Then, 5.2 parts isobutyl chloroformate is added dropwise over a 30 minute period while maintaining the temperature at −15° C. Then, a solution of 9.8 parts L-phenylalanyl-L-leucine benzyl ester in 50 parts dimethylformamide is slowly added at −15° C., and the mixture stirred at this temperature for 30 minutes. The cooling apparatus is removed and the mixture stirred at ambient temperatures for an additional two hours. The product is isolated by diluting the reaction mixture with 10 volumes water and extracting with ethyl acetate. The ethyl acetate extracts are combined, dried over anhydrous sodium sulfate and stripped to dryness under reduced pressure. Purification of the residue by low pressure column chromatography affords N-t-butoxycarbonyl-L-tyrosylglycyl-L-alanyl-L-phenylalanyl-L-leucine benzyl ester.

EXAMPLE 13

18.9 Parts N-t-butoxycarbonyl-L-tyrosylglycyl-L-alanyl-L-phenylalanyl-L-leucine benzyl ester is dissolved in 70 parts methanol and the solution cooled to 10° C. Then, 90 parts by volume of a 1N sodium hydroxide solution is added dropwise with stirring while maintaining the temperature below 20° C. After standing at room temperature for 1 hour, the methanol is removed by evaporation under reduced pressure. The solution is washed once with ethyl ether to remove benzyl alcohol and the aqueous layer acidified with 90 parts by volume of a 1 N hydrochloric acid solution. The solid which results is filtered and washed with water to afford N-t-butoxycarbonyl-L-tyrosylglycyl-L-alanyl-L-phenylalanyl-L-leucine.

The N-t-butoxycarbonyl-L-tyrosylglycyl-L-alanyl-L-phenylalanyl-L-leucine is dissolved in 100 parts dioxane and stirred with a ten-fold excess of 2 N HCl in dioxane at room temperature for 15 minutes. The solvent is then removed under reduced pressure and the residue triturated with ethyl ether. The resulting solid is precipitated from the mixture of methanol and ether to afford L-tyrosylglycyl-L-alanyl-L-phenylalanyl-L-leucine hydrochloride.

The L-tyrosylglycyl-L-alanyl-L-phenylalanyl-L-leucine hydrochloride is dissolved in 250 parts by volume of 20% acetic acid and passed slowly through an IR-45 ion exchange column in the acetate form. The column is washed with 20% acetic acid until no more peptide is eluted. Fractions containing the product are combined and the solvent removed by stripping under reduced pressure at room temperature. The residual glass is dissolved in 75 parts water and lyophilized to give L-tyrosylglycyl-L-alanyl-L-phenylalanyl-L-leucine as a fluffy solid. This compound is represented by the following formula

H—Tyr—Gly—Ala—Phe—Leu—OH

EXAMPLE 14

When an equivalent quantity of N-t-butoxycarbonyl-L-tyrosylglycylsarcosine is substituted for the N-t-butoxycarbonyl-L-tyrosylglycyl-L-alanine of Example 12 and the procedure detailed therein substantially repeated, there is obtained N-t-butoxycarbonyl-L-tyrosylglycylsarcosyl-L-phenylalanyl-L-leucine benzyl ester.

EXAMPLE 15

Repetition of the procedure detailed in Example 13 using an equivalent quantity of N-t-butoxycarbonyl-L-tyrosylglycylsarcosyl-L-phenylalanyl-L-leucine benzyl ester affords L-tyrosylglycylsarcosyl-L-phenylalanyl-L-leucine. This compound is represented by the following formula

H—Tyr—Gly—Sar—Phe—Leu—OH

EXAMPLE 16

When an equivalent quantity of N-t-butoxycarbonyl-L-tyrosyl-L-alanylglycine is substituted for the N-t-butoxycarbonyl-L-tyrosylglycyl-L-alanine of Example 12 and the procedure detailed therein substantially repeated, there is obtained N-t-butoxycarbonyl-L-tyrosyl-L-alanylglycyl-L-phenylalanyl-L-leucine benzyl ester.

EXAMPLE 17

Repetition of the procedure detailed in Example 13 using an equivalent quantity of N-t-butoxycarbonyl-L-tyrosyl-L-alanylglycyl-L-phenylalanyl-L-leucine benzyl ester affords L-tyrosyl-L-alanylglycyl-L-phenylalanyl-L-leucine. This compound is represented by the following formula

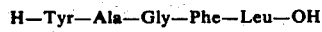
H—Tyr—Ala—Gly—Phe—Leu—OH

EXAMPLE 18

When an equivalent quantity of N-t-butoxycarbonyl-L-tyrosylsarcosylglycine is substituted for the N-t-butoxycarbonyl-L-tyrosylglycyl-L-alanine of Example 12 and the procedure detailed therein substantially repeated, there is obtained N-t-butoxycarbonyl-L-tyrosylsarcosylglycyl-L-phenylalanyl-L-leucine benzyl ester.

EXAMPLE 19

Repetition of the procedure detailed in Example 13 using an equivalent quantity of N-t-butoxycarbonyl-L-tyrosylsarcosylglycyl-L-phenylalanyl-L-leucine benzyl ester affords L-tyrosylsarcosylglycyl-L-phenylalanyl-L-leucine. This compound is represented by the following formula

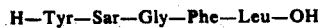
H—Tyr—Sar—Gly—Phe—Leu—OH

EXAMPLE 20

When an equivalent quantity of L-phenylalanyl-L-methionine benzyl ester is substituted for the L-phenylalanyl-L-leucine benzyl ester of Example 12 and the procedure detailed therein substantially repeated, there is obtained N-t-butoxycarbonyl-L-tyrosylglycyl-L-alanyl-L-phenylalanyl-L-methionine benzyl ester.

EXAMPLE 21

Repetition of the procedure detailed in Example 13 using an equivalent quantity of N-t-butoxycarbonyl-L-tyrosylglycyl-L-alanyl-L-phenylalanyl-L-methionine benzyl ester affords L-tyrosylglycyl-L-alanyl-L-phenylalanyl-L-methionine. This compound is represented by the following formula

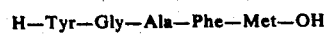
H—Tyr—Gly—Ala—Phe—Met—OH

EXAMPLE 22

When equivalent quantities of N-t-butoxycarbonyl-L-tyrosylglycylsarcosine and L-phenylalanyl-L-methionine benzyl ester are substituted for the N-t-butoxycarbonyl-L-tyrosylglycyl-L-alanine and the L-phenylalanyl-L-leucine benzyl ester, respectively, of Example 12 and the procedure detailed therein substantially repeated, there is obtained N-t-butoxycarbonyl-L-tyrosylglycylsarcosyl-L-phenylalanyl-L-methionine benzyl ester.

EXAMPLE 23

Repetition of the procedure detailed in Example 13 using an equivalent quantity of N-t-butoxycarbonyl-L-tyrosylglycylsarcosyl-L-phenylalanyl-L-methionine benzyl ester affords L-tyrosylglycylsarcosyl-L-phenylalanyl-L-methionine. This compound is represented by the following formula

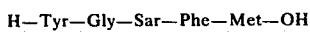
H—Tyr—Gly—Sar—Phe—Met—OH

EXAMPLE 24

When equivalent quantities of N-t-butoxycarbonyl-L-tyrosyl-L-alanylglycine and L-phenylalanyl-L-methionine benzyl ester are reacted according to the procedure detailed in Example 12, there is obtained N-t-butoxycarbonyl-L-tyrosyl-L-alanylglycyl-L-phenylalanyl-L-methionine benzyl ester.

EXAMPLE 25

Repetition of the procedure detailed in Example 13 using an equivalent quantity of N-t-butoxycarbonyl-L-tyrosyl-L-alanylglycyl-L-phenylalanyl-L-methionine benzyl ester yields L-tyrosyl-L-alanylglycyl-L-phenylalanyl-L-methionine represented by the following formula

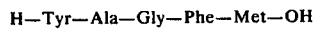
H—Tyr—Ala—Gly—Phe—Met—OH

EXAMPLE 26

When equivalent quantities of N-t-butoxycarbonyl-L-tyrosylsarcosylglycine and L-phenylalanyl-L-methionine benzyl ester are reacted according to the procedure detailed in Example 12, there is obtained N-t-butoxycarbonyl-L-tyrosylsarcosylglycyl-L-phenylalanyl-L-methionine benzyl ester.

EXAMPLE 27

Repetition of the procedure detailed in Example 13 using an equivalent quantity of N-t-butoxycarbonyl-L-tyrosylsarcosylglycyl-L-phenylalanyl-L-methionine benzyl ester yields L-tyrosylsarcosylglycyl-L-phenylalanyl-L-methionine represented by the following formula

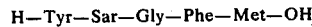
H—Tyr—Sar—Gly—Phe—Met—OH

EXAMPLE 28

When an equivalent quantity of N-t-butoxycarbonyl-L-tyrosyl-5-aminopentanoic acid is substituted for the N-t-butoxycarbonyl-L-tyrosylglycyl-L-alanine of Example 12 and the procedure detailed therein substantially repeated, there is obtained N-t-butoxycarbonyl-L-tyrosyl-5-aminopentanoyl-L-phenylalanyl-L-leucine benzyl ester.

EXAMPLE 29

Repetition of the procedure detailed in Example 13 using an equivalent quantity of N-t-butoxycarbonyl-L-tyrosyl-5-aminopentanoyl-L-phenylalanyl-L-leucine benzyl ester affords L-tyrosyl-5-aminopentanoyl-L-phenylalanyl-L-leucine represented by the following formula

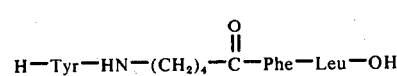
H—Tyr—HN—(CH₂)₄—C—Phe—Leu—OH

EXAMPLE 30

When an equivalent quantity of N-t-butoxycarbonyl-L-tyrosyl-p-aminobenzoic acid is substituted for the N-t-butoxycarbonyl-L-tyrosylglycyl-L-alanine of Example 12 and the procedure detailed therein substantially repeated, there is obtained N-t-butoxycarbonyl-L-tyrosyl-p-aminobenzoyl-L-phenylalanyl-L-leucine benzyl ester.

EXAMPLE 31

Repetition of the procedure detailed in Example 13 using an equivalent quantity of N-t-butoxycarbonyl-L-tyrosyl-p-aminobenzoyl-L-phenylalanyl-L-leucine benzyl ester affords L-tyrosyl-p-aminobenzoyl-L-phenylalanyl-L-leucine, represented by the following formula

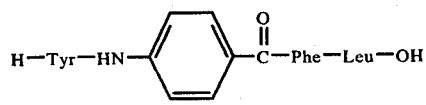

EXAMPLE 32

When equivalent quantities of N-t-butoxycarbonyl-L-tyrosyl-5-aminopentanoic acid and L-phenylalanyl-L-methionine benzyl ester are reacted according to the procedure of Example 12, there is obtained N-t-butoxycarbonyl-L-tyrosyl-5-aminopentanoyl-L-phenylalanyl-L-methionine benzyl ester.

EXAMPLE 33

Repetition of the procedure detailed in Example 13 using an equivalent quantity of N-t-butoxycarbonyl-L-tyrosyl-5-aminopentanoyl-L-phenylalanyl-L-methionine benzyl ester affords L-tyrosyl-5-aminopentanoyl-L-phenylalanyl-L-methionine, represented by the following formula

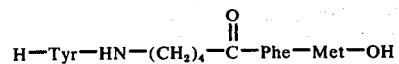
H—Tyr—HN—(CH₂)₄—C—Phe—Met—OH

EXAMPLE 34

When equivalent quantities of N-t-butoxycarbonyl-L-tyrosyl-p-amino benzoic acid and L-phenylalanyl-L-methionine benzyl ester are reacted according to the procedure of Example 12, there is obtained N-t-butoxycarbonyl-L-tyrosyl-p-aminobenzoyl-L-phenylalanyl-L-methionine benzyl ester.

EXAMPLE 35

Repetition of the procedure detailed in Example 13 using an equivalent quantity of N-t-butoxycarbonyl-L-tyrosyl-p-aminobenzoyl-L-phenylalanyl-L-methionine benzyl ester yields L-tyrosyl-p-aminobenzoyl-L-phenylalanyl-L-methionine. This compound is represented by the following formula

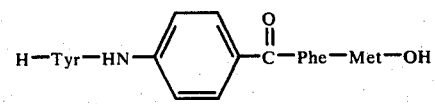

EXAMPLE 36

When equivalent quantities of N-t-butoxycarbonyl-D-tyrosylglycyl-D-alanine and D-phenylalanyl-D-leucine benzyl ester are substituted for the N-t-butoxycarbonyl-L-tyrosylglycyl-L-alanine and L-phenylalanyl-L-leucine benzyl ester, respectively in Example 12 and the procedure detailed therein substantially repeated, there is obtained N-t-butoxycarbonyl-D-tyrosylglycyl-D-alanyl-D-phenylalanyl-D-leucine benzyl ester.

EXAMPLE 37

Repetition of the procedure detailed in Example 13 using an equivalent quantity of N-t-butoxycarbonyl-D-tyrosylglycyl-D-alanyl-D-phenylalanyl-D-leucine benzyl ester affords D-tyrosylglycyl-D-alanyl-D-phenylalanyl-D-leucine. This compound is represented by the following formula

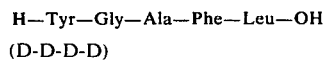

H—Tyr—Gly—Ala—Phe—Leu—OH
(D-D-D-D)

EXAMPLE 38

When equivalent quantities of N-t-butoxycarbonyl-DL-tyrosylglycyl-DL-alanine and DL-phenylalanyl-DL-leucine benzyl ester are substituted for the N-t-butoxycarbonyl-L-tyrosylglycyl-L-alanine and L-phenylalanyl-L-leucine benzyl ester, respectively in Example 12 and the procedure detailed therein substantially repeated, there is obtained N-t-butoxycarbonyl-DL-tyrosylglycyl-DL-alanyl-DL-phenylalanyl-DL-leucine benzyl ester.

EXAMPLE 37

Repetition of the procedure detailed in Example 13 using an equivalent quantity of N-t-butoxycarbonyl-DL-tyrosylglycyl-DL-alanyl-DL-phenylalanyl-DL-leucine benzyl ester affords DL-tyrosylglycyl-DL-alanyl-DL-phenylalanyl-DL-leucine. This compound is represented by the following formula H—Tyr—Gly—Ala—Phe—Leu—OH
(DL—DL—DL—DL)

EXAMPLE 38

Substitution of an equivalent amount of α-aminoisobutyric acid benzyl ester for the L-alanine benzyl ester of Example 3, and substantial repetition of the procedure detailed therein, affords glycyl-α-aminoisobutyric acid benzyl ester hydrochloride.

EXAMPLE 39

Substitution of an equivalent amount of N-t-butoxycarbonyl-N-aminoisobutyric acid 2,4,5-trichlorophenyl ester for the N-t-butoxycarbonyl-L-alanine 2,4,5-trichlorophenyl ester of Example 5 and substantial repetition of the procedure detailed therein, affords α-aminoisobutyrylglycine benzyl ester hydrochloride.

EXAMPLE 40

Repetition of the procedure of Example 7 substituting an equivalent amount of glycyl-α-aminoisobutyric acid benzyl ester hydrochloride or α-aminoisobutyrylglycine benzyl ester hydrochloride for the glycyl-L-alanine benzyl ester hydrochloride affords N-t-butoxycarbonyl-L-tyrosylglycyl-α-aminoisobutyric acid or N-t-butoxycarbonyl-L-tyrosyl-α-aminoisobutyrylglycine, respectively.

EXAMPLE 41

When an equivalent quantity of N-t-butoxycarbonyl-L-tyrosylglycyl-α-aminoisobutyric acid or N-t-butoxycarbonyl-L-tyrosyl-α-aminoisobutyrylglycine is substituted for the N-t-butoxycarbonyl-L-tyrosylglycyl-L-alanine of Example 12, and the procedure detailed therein substantially repeated, there is obtained N-t-butoxycarbonyl-L-tyrosylglycyl-α-aminoisobutyryl-L-phenylalanyl-L-leucine benzyl ester or N-t-butoxycarbonyl-L-tyrosyl--α-aminoisobutyrylglycyl-L-phenylalanyl-L-leucine benzyl ester, respectively.

EXAMPLE 42

Repetition of the procedure detailed in Example 13 using an equivalent quantity of N-t-butoxycarbonyl-L-tyrosyl-glycyl-α-aminoisobutyryl-L-phenylalanyl-L-methionine benzyl ester or N-t-butoxycarbonyl-L-tyrosyl-α-aminoisobutyrylglycyl-L-phenylalanyl-L-methionine benzyl ester affords L-tyrosylglycyl-α-aminoisobutyryl-L-phenylalanyl-L-leucine or L-tyrosyl-α-aminoisobutyrylglycyl-L-phenylalanyl-L-leucine, respectively.

EXAMPLE 43

When equivalent quantities of N-t-butoxycarbonyl-L-tyrosylglycyl-α-aminoisobutyric acid and L-phenylalanyl-L-methionine benzyl ester are substituted for the N-t-butoxycarbonyl-L-tyrosylglycyl-L-alanine and L-phenylalanine-L-leucine benzyl ester, respectively, of Example 12, and the procedure detailed therein substantially repeated, there is obtained N-t-butoxycarbonyl-L-tyrosylglycyl-α-aminoisobutyryl-L-phenyl-alanyl-L-methionine benzyl ester.

EXAMPLE 44

When equivalent quantities of N-t-butoxycarbonyl-L-tyrosyl-α-aminoisobutyrylglycine and L-phenylalanyl-L-methionine benzyl ester are substituted for the N-t-butoxy-carbonyl-L-tyrosylglycyl-L-alanine and L-phenylalanine-L-leucine benzyl ester, respectively, of Example 12, and the procedure detailed therein substantially repeated, there is obtained N-t-butoxycarbonyl-L-tyrosyl-α-aminoisobutyrylglycyl-L-phenylalanyl-L-methionine benzyl ester.

EXAMPLE 45

Repetition of the procedure detailed in Example 13 using an equivalent quantity of N-t-butoxycarbonyl-L-tyrosyl-glycyl-α-aminoisobutyryl-L-phenylalanyl-L-methionine benzyl ester or N-t-butoxycarbonyl-L-tyrosyl-α-aminoisobutyrylglycyl-L-phenylalanyl-L-methionine benzyl ester affords L-tyrosylglycyl-α-aminoisobutyryl-L-phenylalanyl-L-methionine or L-tyrosyl-α-aminoisobutyrylglycyl-L-phenylalanyl-L-methionine, respectively.

What is claimed is:

1. A compound of the formula

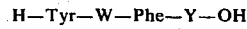

H—Tyr—W—Phe—Y—OH        (I)

wherein Y is Leu or Met; W is selected from the group consisting of
—Aib—Gly—,
—Ala—Gly—,
—Sar—Gly—,
—Gly—Aib—, —Gly—Ala—,
—Gly—Sar—,

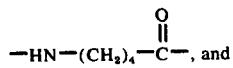, and

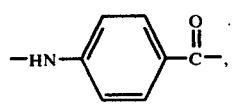

and the stereochemical configuration of each of the optically active amino acid residues is D, L or DL.

2. A compound according to claim 1 of the formula

H—Tyr—W—Phe—Y—OH    (II)

wherein Y is Leu or Met; W is selected from the group consisting of
—Aib—Gly—,
—Ala—Gly—,
—Sar—Gly—,
—Gly—Aib—,
—Gly—Ala—,
—Gly—Sar—,

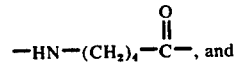, and

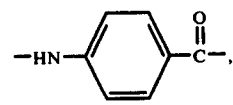

and the stereochemical configuration of each of the optically active amino acid residues is L.

3. A compound according to claim 1 of the formula

H—Tyr—Z—Gly—Phe—Y—OH wherein Z is Aib, Ala or Sar; Y is Leu or Met; and the stereochemical configuration of each of the optically active amino acid residues is L.

4. A compound according to claim 1 of the formula

H—Tyr—Gly—Z—Phe—Y—OH wherein Z is Aib, Ala or Sar; Y is Leu or Met; and the stereochemical configuration of each of the optically active amino acid residues is L.

5. A compound according to claim 1 of the formula

H—Tyr—W—Phe—Y—OH wherein Y is Leu or Met; W is

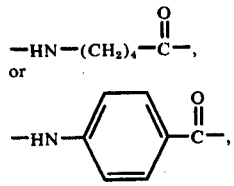

and the stereochemical configuration of each of the optically active amino acid residues is L.

6. The compound according to claim 1 which is L-tyrosyl-L-alanylglycyl-L-phenylalanyl-L-methionine.
7. The compound according to claim 1 which is L-tyrosyl-L-alanylglycyl-L-phenylalanyl-L-leucine.
8. The compound according to claim 1 which is L-tyrosylsarcosylglycyl-L-phenylalanyl-L-methionine.
9. The compound according to claim 1 which is L-tyrosylsarcosylglycyl-L-phenylalanyl-L-leucine.
10. The compound according to claim 1 which is L-tyrosylglycyl-L-alanyl-L-phenylalanyl-L-methionine.
11. The compound according to claim 1 which is L-tyrosylglycyl-L-alanyl-L-phenylalanyl-L-leucine.
12. The compound according to claim 1 which is L-tyrosylglycylsarcosyl-L-phenylalanyl-L-methionine.
13. The compound according to claim 1 which is L-tyrosylglycylsarcosyl-L-phenylalanyl-L-leucine.
14. The compound according to claim 1 which is L-tyrosyl-5-aminopentanoyl-L-phenylalanyl-L-methionine.
15. The compound according to claim 1 which is L-tyrosyl-5-aminopentanoyl-L-phenylalanyl-L-leucine.
16. The compound according to claim 1 which is L-tyrosyl-p-aminobenzoyl-L-phenylalanyl-L-methionine.
17. The compound according to claim 1 which is L-tyrosyl-p-aminobenzoyl-L-phenylalanyl-L-leucine.
18. The compound according to claim 1 which is L-tyrosyl-α-aminoisobutyrylglycyl-L-phenylalanyl-L-methionine.
19. The compound according to claim 1 which is L-tyrosyl-α-aminoisobutyrylglycyl-L-phenylalanyl-L-leucine.
20. The compound according to claim 1 which is L-tyrosylglycyl-α-aminoisobutyryl-L-phenylalanyl-L-methionine.
21. The compound according to claim 1 which is L-tyrosylglycyl-α-aminoisobutyryl-L-phenylalanyl-L-leucine.
22. The compound according to claim 1 which is D-tyrosylglycyl-D-alanyl-D-phenylalanyl-D-leucine.
23. The compound according to claim 1 which is DL-tyrosylglycyl-DL-alanyl-DL-phenylalanyl-DL-leucine.

* * * * *

Notice of Adverse Decision in Interference

In Interference No. 99,833 involving Patent No. 4,028,319, D. A. Jones, Jr., J. M. Schlatter, R. A. Mikulec, J. A. Reuter, and R. H. Mazur, 2 AND 3-SUBSTITUTED ENKEPHALINS, final judgment adverse to the patentees was rendered July 19, 1978, as to claim 6.

[*Official Gazette October 17, 1978.*]

Disclaimer 4,028,319.—*David A. Jones, Jr.*, Evanston; *James M. Schlatter*, Glenview; *Richard A. Mikulec*, Chicago; *Judith A. Reuter*, Skokie, and *Robert H. Mazur*, Deerfield, Ill. 2 and 3-SUBSTITUTED ENKEPHALINS. Patent dated June 7, 1977. Disclaimer filed Nov. 30, 1981, by the assignee, *G. D. Searle & Co.*

Hereby enters this disclaimer to claims 1-3, 8 and 9 of said patent.

[*Official Gazette Feb. 2, 1982.*]

Notice of Adverse Decision in Interference

In Interference No. 101,285, involving Patent No. 4,028,319, D. Jones, J. Schlatter, R. Mikulec, J. Reuter and R. Mazur, 2 AND 3-SUBSTITUTED ENKEPHALINS, final judgment adverse to the patentees was rendered Feb. 27, 1985, as to claims 4, 7, 10, 11 and 12.

[*Official Gazette April 30, 1985.*]